United States Patent
Heine

(10) Patent No.: US 6,174,664 B1
(45) Date of Patent: Jan. 16, 2001

(54) SCREENING METHOD FOR INFLAMMATORY DISEASES USING NEUTROPHIL DEFENSINS AND LACTOFERRIN

(75) Inventor: Robert Phillips Heine, Pittsburgh, PA (US)

(73) Assignee: University of Pittsburgh, Pittsburgh, PA (US)

( * ) Notice: Under 35 U.S.C. 154(b), the term of this patent shall be extended for 0 days.

(21) Appl. No.: 09/305,594

(22) Filed: May 5, 1999

Related U.S. Application Data

(63) Continuation-in-part of application No. 08/796,666, filed on Feb. 5, 1997, now Pat. No. 5,972,594.

(51) Int. Cl.$^7$ ......................... G01N 33/53; G01N 33/48; C12Q 1/00; A61K 38/00

(52) U.S. Cl. .................................... 435/4; 435/4; 435/7.1; 435/7.92; 435/962; 435/970; 435/973; 436/63; 436/802; 436/805; 436/811; 514/12

(58) Field of Search .................................... 435/7.1, 7.92, 435/4, 962, 973, 970; 436/63, 802, 805, 811; 514/12

(56) References Cited

U.S. PATENT DOCUMENTS

| | | |
|---|---|---|
| 4,705,777 | 11/1987 | Lehrer et al. . |
| 5,124,252 * | 6/1992 | Guerrant et al. .................... 435/7.24 |
| 5,126,257 | 6/1992 | Gabay et al. . |
| 5,459,235 | 10/1995 | Selsted et al. . |
| 5,516,702 | 5/1996 | Senyei et al. . |
| 5,556,782 | 9/1996 | Cooper et al. . |
| 5,670,133 | 9/1997 | Zamora . |

OTHER PUBLICATIONS

Prieto, J.A., Panyutich, A.V., and Heine, R.P., "Neutrophil Activation in Preclampsia: Are Defensins and Lactoferrin Elevated in Preelamptic Patients?,"The Journal of Reproductive Medicine, vol. 42 (No. 1), p. 29–32, (Jan. 1997).

Qu, X.D., Harwig, S.S.L., Oren, A., Shafer, W.M., and Lehrer, R.I., "Susceptibility of Neisseria gonnorrhoeae to Protegrins," Infection and Immunity, vol. 64 (No. 4), p. 1240–1245, (1996).

Rebelo, I., Carvahalo–Guerra, F., Pereira–Leite, L., and Quintanilha, A., "Comparative study of lactoferrin and other blood markers of inflammatory stress between preeclamptic and normal pregnancies," European Journal of Obstetrics & Gynecology and Reproductive Biology, vol. 64, p. 167–173, (Feb. 1996).

Rein, M.F., Shih, L.M., Miller, J.R., and Guerrant, R.L., "Use of a Lactoferrin Assay in the Differential Diagnosis of Female Genital Tract Infections and Implications for the Pathophysiology of Bacterial Vaginosis," Sexually Transmitted Diseases, p. 517–521, (Nov.–Dec. 1996).

Panyutich, A.V., Panyutich, E.A., Krapivin, V.A., Baturevich, E.A., and Ganz, T., "Plasma defensin concentrations are elevated in patients with septicema or bacterial meningitis," J. Lab. Clin. Med., vol. 122 (No. 2), p. 202–207, (Aug. 1993).

Panyutich, A.V., Voitenok, N.I., Lehrer, R.I., and Ganz, T., "An enzyme immunoassay for human defensins," Journal of Immunological Methods, vol. 141(2), p. 149–155, (1991).

Heine, R.P., Wiesenfeld, H. Mortimer, L. and Greig, P.C., "Amniotic Fluid Defensins: Potential Markers of Subclinical Intrauterine Infection," Clinical Infectious Diseases, vol. 27, p. 513–518, (Sep. 1998).

Arao, S., Matsuura, S., Nonomura, M., Miki, K., Kabasawa, K. and Nakanishi, H., "Measurement of Urinary Lactoferrin as a Marker of Urinary Tract Infection," Journal of Clinical Microbiology, vol. 37 (No. 3), p. 553–557, (Mar. 1999).

Heller, K.A., Greig, P.C., and Heine, R.P., "Amniotic–Fluid Lactoferrin: A Marker for Subclinical Intraamniotic Infection Prior to 32 Weeks Gestation," Infectious Diseases in Obstetrics and Gynecology, vol. 3, p. 179–183, 1996.

Prieto, L.A., Panyutich, A.V., and Heine, R.P., "Human Neutrophil Defensins Are Elevated in Plasma of Preeclamptic Patients," SPO Abstracts (Presented Feb. 5, 1996), American Journal of Obstetrics and Gynecology, p. 452, (Jan. 1996).

Heine, R.P., Wiesenfeld, H.C., Krohn, M.A., Hillier, S.L., Crowe, D.S. and Landers, D.V., "Vaginal Fluid Lactoferrin Levels Are Elevated In Women With Lower Reproductive Tract Infections," Infectious Diseases In Obstetrics and Gynecology, Abstracts, p. 79–80, (Sep. 1998).

\* cited by examiner

*Primary Examiner*—Long V. Le
*Assistant Examiner*—Gailene R. Gabel
(74) *Attorney, Agent, or Firm*—Thorp Reed & Armstrong, LLP

(57) ABSTRACT

The present invention provides a relatively accurate, rapid and economical method of screening a patient for the presence of inflammatory diseases such as an intraamniotic infection, bacterial meningitis and the sexually transmitted diseases; gonorrhea, chlamydia and trichomoniasis. The method of the present invention involves measuring the concentration of neutrophil defensins HNP1–3 and the concentration of lactoferrin, found in a bodily fluid, tissue or a combination thereof, adding these two concentrations together to yield a summed total, and correlating the measured summed total to known summed totals to give an indication of whether the patient is at risk of suffering from inflammatory diseases such as an intraamniotic infection, bacterial meningitis or the sexually transmitted diseases; gonorrhea, chlamydia and trichomoniasis.

22 Claims, No Drawings

SCREENING METHOD FOR INFLAMMATORY DISEASES USING NEUTROPHIL DEFENSINS AND LACTOFERRIN

Related Application

This patent application is a continuation-in-part patent application of U.S. application, Ser. No. 08/796,666 now U.S. Pat. No. 5,972,594, filed by Robert Phillips Heine on Feb. 5, 1997 and entitled: METHOD AND APPARATUS FOR SCREENING FOR REPRODUCTIVE TRACT INFLAMMATION AND PREECLAMPSIA USING NEUTROPHIL DEFENSINS, the contents of which are incorporated herein by reference.

STATEMENT REGARDING FEDERALLY-SPONSORED RESEARCH

The research that led to this invention was partially supported by the government under Grant No. DAND 17-96-1-6298 awarded by the United States Department of Defense.

The government has certain rights in the invention.

BACKGROUND OF THE INVENTION

1. Field of the Invention

The present invention relates to a method of screening for inflammatory diseases in a patient. More particularly, this invention concerns the method of screening a patient for the presence of inflammatory diseases such as an intraamniotic infection, bacterial meningitis and the sexually transmitted diseases; gonorrhea, chlamydia and trichomoniasis, by utilizing neutrophil defensins and lactoferrin, found in a bodily fluid, a tissue or a combination thereof, to give an indication of whether the patient is at risk of suffering from one or more such inflammatory diseases.

2. Description of Related Art

The methods of disease detection may be divided into two general types: diagnosis and screening. Diagnosis is the method whereby a physician determines the nature of a disease based upon the patient's signs and symptoms. Screening is the method of suggesting the presence, or the absence, of a particular disease, or class of diseases, in a patient. When a screening test indicates that a patient does not have a disease, in many cases the need for further diagnostic testing has been eliminated. Used in this manner, screening saves money for patients, health insurance companies and government health programs by precluding the unwarranted diagnostic testing of people shown not to suffer from the disease or class of diseases. To be effective in reducing unnecessary diagnostic testing, however, a screening method must be widely used. In order that a screening method is widely used, the screening test should be relatively accurate, quick, and economical to use.

In addition, screening provides a way for patients to avoid the cost and discomfort associated with the more invasive procedures often necessary to collect the samples required for diagnostic testing. The following are some of the conventional methods used for screening and diagnosing inflammatory conditions such as an intraamniotic infection, bacterial meningitis, and the sexually transmitted diseases; gonorrhea, chlamydia and trichomoniasis.

a. Intraamniotic Infections

An intraamniotic infection is an infection of the amnion or of the amniotic fluid by any pathogen. It is thought to be a significant cause of idiopathic preterm labor, which results in preterm deliveries. The typical screening procedure for an intraamniotic infection involves the physician empirically identifying women in preterm labor. Unfortunately, the majority of women with preterm labor do not have overt signs or symptoms of intraamniotic infection, such as fever, increased heart rate and abdominal tenderness between contractions.

The standard test for diagnosing an intraamniotic infection involves the physician obtaining an amniotic fluid sample from the patient via amniocentesis. This is followed by growth of a culture from the extracted fluid. Diagnosis is both costly and time consuming, because a physician must perform the amniocentesis procedure to procure the necessary sample and skilled laboratory personnel are needed to grow and analyze the culture. Growth of the specimen requires at least 24 hours, which significantly delays treatment. Further, diagnosis is often negative in cases where there is significant placental infection or inflammation. Also, the procedure itself can present a risk to the fetus, and discomfort to the mother. Therefore, many clinicians diagnose intraamniotic infections solely based on the inability to stop labor with tocolytics. Recent evidence linking infection to cerebral palsy suggests that this practice may potentially be harmful. Clearly, more rapid means of identifying patients with intraamniotic infection are needed.

b. Bacterial Meningitis

Bacterial meningitis afflicts approximately 10,000 people annually. The typical screening method for bacterial meningitis involves empirical observation by the physician of the presence of the following symptoms in children: fever with temperature, instability, 35 irritability or lethargy, refusal to feed, vomiting and diarrhea and respiratory distress. In adults, the physician looks for: fever, headache, meningismus or irritation of the lining of the brain and altered mental status. Complications of bacterial meningitis can include death and neurologic sequalae in approximately 10–20% of patients. Figures are higher in immunosuppressed patients such as newborn babies. Fortunately, early diagnosis and treatment will reduce these complications.

Bacterial meningitis is typically diagnosed by first obtaining a sample of cerebrospinal fluid (CSF) from the patient by means of a lumbar puncture. This sample is then cultured and stained for Gram positive bacteria. Also, measurements of white blood cells, glucose and protein in the cerebrospinal fluid can be made. Deviations in these parameters from normal levels can be used by the physician to diagnose bacterial meningitis. A CSF white blood cell count greater than $1000/\mu L$, a CSF glucose level less than 30 mg/dL and a CSF protein level greater than 100 mg/dL, can be used alone or in combination to diagnose bacterial meningitis in a patient. The major drawback to using these tests individually to diagnose bacterial meningitis lies in their low sensitivity. While positive Gram stains have an eighty-four percent (84%) sensitivity, white blood cell counts have a sensitivity of only fifty-three percent (53%), and glucose levels have only a fifty-eight percent (58%) sensitivity. Protein levels have a sensitivity of ninety percent (90%). Therefore, these tests are typically utilized in combination, with an abnormality in any one test being used to predict bacterial meningitis. If all four tests are used in this manner, they can result in approximately a ninety-five percent (95%) sensitivity. (See Table 2) Performing all these tests, however, can also result in more expense being borne by the patient because a physician must perform the lumbar puncture and a competent laboratory must conduct the testing. Making a diagnosis in this manner can also result in a longer time being required because the physician may have to await the results from four tests before being certain that there is an abnormality in at least one test.

c. Sexually Transmitted Diseases

The typical screening method for sexually transmitted diseases involves the physician noting the patient complaining of painful or difficult urination, called dysuria, and abnormal discharge. The physician then checks the patient for redness, swelling or sores on or about the genitalia. Additional screening methods include using the leukocyte esterase dipstick or neutrophil quantification on Gram stain or wet smear. Unfortunately, these methods have sensitivities of thirty-three percent (33%) to eighty percent (80%) with specificities of fifty percent (50) to eighty percent (80%) thereby making them less than ideal for routine clinical use.

Another type of screening method for sexually transmitted diseases, employed by the World Health Organization and by some Third World countries, involves the use of an algorithm comprising a series of questions. Because this screening method is based solely on the patient's answers to questions, which may be either inaccurate or untruthful, and not on any physical assessment of the patient by a physician, the degree of error is likely to be quite high. Further, because of the scarcity of resources in Third World countries, no other test is performed in those cases where the answers do not suggest the presence of an infection, thereby neglecting many patients who are infected.

Several diagnostic tests for sexually transmitted diseases are readily available in the United States and other developed nations. The most accurate diagnostic techniques are PCR and LCR, both of which amplify the amount of pathogenic microbial genetic material in a patient specimen to detectable levels. The use of PCR and LCR is limited by the expense involved in having a physician collect a specimen from the patient and the costs for a proficient facility to perform the necessary lab work.

(1) Gonorrhea

Gonorrhea is caused by the gonococcal bacterium Neisseria gonorrheae. If undetected and therefore untreated, gonorrhea can cause postgonococcal nonspecific urethritis, epididymitis, pelvic inflammatory disease, arthritis and even death. There were one million (1,000,000) cases of gonorrhea reported in the United States and approximately one-hundred- twenty million (120,000,000) cases worldwide. One method commonly employed in diagnosing gonorrhea involves performing a Gram-stained smear on a scraping taken from the patient. A culture is required for females because a Gram-stain is considered less reliable for them. There are several disadvantages to the use of this diagnostic method. First, it is costly because it requires a physician take the sample required for the test. Second, it is time consuming because a culture must be grown from the sample. Third, it requires a skilled laboratory to conduct the test, thereby further increasing the cost to the patient. And finally, it requires that an uncomfortable, invasive procedure be performed on the patient to obtain the needed specimen. This method has a sensitivity of about eighty-five percent (85%) to ninety percent (90%).

(2) Chlamydia

Chlamydia is caused by the bacterium Chlamydia trachomatous. If undetected and therefore untreated, chlamydia can cause pelvic inflammatory disease, chronic pelvic pain, ectopic pregnancy and infertility. In addition, undetected chlamydia is thought to cause about fifty percent (50%) of the nonspecific sexually transmitted infections, including nongonococcal urethritis and nonspecific urethritis. Each year, there are approximately four million (4,000,000) cases of chlamydia reported in the United States and seventy-two million (72,000,000) cases reported worldwide.

A standard method used in diagnosing chlamydia involves obtaining a scraping from the patient, which in women is taken from the endocervix. The scraping is then placed in a sterile nutritive medium and observed under a microscope for signs of microbial growth and the disease organism. A limitation on the use of this diagnostic method is the high cost, because a physician must procure the sample and skilled laboratory personnel must perform the test. Another limitation is the prolonged incubation time required to grow a culture. Also, it requires that an uncomfortable, invasive procedure be performed on the patient to gather the desired specimen. This method has a sensitivity of about seventy-five percent (75%) to eighty-five percent (85%).

The pathogenic microbial proteins that cause chlamydia may be detected in an endocervical scraping by direct fluorescent antibody testing (DFA) and enzyme-linked immunosorbent assay (ELISA), and by serological tests involving either complement fixation or microimmunifluorescence. These antigen detection tests for chlamydia are easily performed and are less costly than cultures. However, these methods are limited by a lower sensitivity than cultures and a low positive predictive value in low prevalence populations.

(3) Trichomoniasis

Trichomoniasis is caused by the flagellate protozoan Trichomonas vaginalis. If undetected and therefore untreated, trichomoniasis can cause vaginitis, urethritis, cystitis and prostatitis. Trichomoniasis afflicts approximately four million (4,000,000) people in the United States and one-hundred-eighty million (180,000,000) people worldwide. The "gold standard" test used to diagnose trichomoniasis is culture on a specimen taken from the posterior fornix. While this test is highly sensitive, its use is hindered by laboratory availability. Therefore, trichomoniasis is more commonly diagnosed by wet mount microscopy conducted on a similar specimen. The disadvantage of using wet mount microscopy to detect trichomoniasis is that this test has a low sensitivity of only about fifty percent (50%).

The newer techniques of PCR and LCR can detect sexually transmitted diseases by relying on nucleic acid amplification with subsequent detection. These tests are considered the most accurate diagnostic methods available. Nucleic acid amplification is presently commercially available for *Chlamydia trachomatous* and *Neisseria gonorrhea* and is under development for *Trichomonas vaginalis*. The important feature of these methods is their reliance on the mere presence of a small amount of the infectious organism, not on its viability. This reliance, on only the presence of the organism, makes it possible for the patient to self-collect a specimen such as urine and/or a swab from the vaginal introitus. The patient can then deposit the sample with a testing laboratory, by whatever means convenient, with no decrease in testing sensitivity. While these newer testing methods remove the requirement, and therefore the cost, of a physician being needed to obtain the sample, a major drawback associated with these methods is the increased cost of the diagnostic test itself.

Limitations in the above-mentioned methods of screening and diagnosing inflammatory conditions include; the inaccuracy of the methods, the need for a competent laboratory to perform the diagnostic test, delay between testing and results, and the necessity that a physician, possibly a high-priced specialist, be employed to collect the sample required for testing. All these factors combine to result in greater expense to the patient. Nowhere in the related art is there disclosed or suggested a method of screening for such inflammatory conditions which is relatively accurate, quick and inexpensive.

Therefore, there is a definite need for such a method of screening for inflammatory diseases such as an intraamniotic infection, bacterial meningitis, and the sexually transmitted diseases; gonorrhea, chlamydia and trichomoniasis, which is relatively accurate, quick, and economical, so that a greater number of people can be reliably and rapidly screened for these diseases. This screening would result in the appropriate diagnostic tests being utilized much more efficiently than is currently the case. Also, the patients thereby diagnosed could receive the correct medical treatment earlier in the pathology of the disease, when such intervention is likely to be more effective and less costly.

Neutrophils, or polymorphonuclear leukocytes, are specialized white blood cells, which are recruited to the site of a microbial invasion such as an infection. Once there, these neutrophils engulf and consume the invading microbes. The neutrophils digest the invaders by releasing toxic, antimicrobial peptides such as the defensins and lactoferrin into the phagosome. Defensins and lactoferrin are abundant in patients with inflammatory diseases such as an intraamniotic infection, bacterial meningitis and the sexually transmitted diseases; gonorrhea, chlamydia and trichomoniasis.

Defensins, also known as neutrophil peptides (NP), are a family of small, cationic, cysteine-rich antimicrobial peptides. In humans, they are designated "HNP." The predominant forms are HNP1, HNP2 and HNP3, which are herein referred to as the aggregate, "defensins HNP1-3." Defensins are found in the primary granules of the neutrophil. The defensins constitute greater than five percent (5%) of the total cellular protein and thirty percent (30%) to fifty percent (50%) of the total granule protein. Neutrophil defensins are highly stable to prolonged storage and are resistant to proteolysis and pH effects. The defensins increase membrane permeability by forming channels in the outer membranes of microbial cells and targeted host cells. Studies have shown that neutrophil defensins HNP1-3 are elevated in the blood plasma of patients with either bacterial meningitis or septicemia. This type of method is described in greater detail in, *Journal of Laboratory and Clinical Medicine*, 122: 202–207 (1993). Measuring the concentrations of other defensins such as HNP4, human defensins HD-5 and HD-6, and the human β -defensins, HBD-1 and HBD-2, can also be done, either individually, or in combination with each other and/or the defensins HNP1-3, in accordance with the present invention.

Lactoferrin is an iron-binding, antimicrobial glycoprotein found in the secondary granules of the neutrophil and in endothelial tissues throughout the body. Like the defensins, lactoferrin is resistant to proteolysis and pH effects and can be stored for a prolonged period. Lactoferrin acts as a bacteriostatic agent by inhibiting bacterial growth. It does this by competing with bacteria for iron. Lactoferrin is also thought to possess a direct bactericidal activity that makes microbes more susceptible to attack by other antimicrobial peptides such as the defensins. Studies have shown that lactoferrin levels are elevated in the cerebrospinal fluid of patients with bacterial or viral meningitis. This type of method is described in more detail in, *Acta Paediatrica Scandinavica* 76: 987–988 (1987).

The present invention provides a method of evaluating, i.e., diagnosing and/or screening a patient for inflammatory diseases such as an intraamniotic infection, bacterial meningitis and the sexually transmitted diseases; gonorrhea, chlamydia and trichomoniasis. The present invention accomplishes this screening by measuring the concentration of neutrophil defensins, preferably neutrophil defensins HNP1-3, and the concentration of lactoferrin, found in a bodily fluid, a tissue or a combination thereof, adding these two concentrations together to yield a summed total or creating a threshold value of a dipstick test which both lactoferrin and defensins must meet. This measured sum total or ascertainment of a threshold value will give an indication of whether the patient is at risk of suffering from inflammatory diseases such as an intraamniotic infection, bacterial meningitis or the sexually transmitted diseases; gonorrhea, chlamydia and trichomoniasis. Such a screening method, as is herein provided, has never been disclosed or suggested in the prior art. The advantages and benefits of the present invention will be apparent from the Detailed Description of the Invention herein below.

BRIEF DESCRIPTION OF THE FIGURES

The present invention will now be described for purposes of illustration and not limitation in conjunction with the following tables, wherein:

Table 1 summarizes data for the combined defensins HNP1-3 and lactoferrin levels obtained in amniotic fluid samples for patients with a positive culture (1-A) and positive culture and/or positive histology (1-B) at less than 32 weeks gestation;

Table 2 summarizes data from measurements of cerebrospinal fluid samples, for standard CSF parameters, defensins HNP1-3 alone, lactoferrin alone, and defensins HNP1-3+ lactoferrin; and Table 3 summarizes data from vaginal fluid samples for patients presenting with lower reproductive tract symptoms.

DETAILED DESCRIPTION OF THE INVENTION

The preferred method of measuring defensins HNP1-3, and of measuring lactoferrin, in a sample of bodily fluid, a tissue or a combination thereof, is by the antigen detection method termed enzyme-linked immunosorbent assay (ELISA). ELISA is preferred because of its enhanced sensitivity to small amounts of peptides, and is further described in *European Journal of Immunology*, Volume 6 at p. 292, (1976).

The monoclonal antibodies used for the ELISA of defensins HNP1-3 can be prepared, using hybridoma preparation techniques, from known secreting hybridomal cell lines, preferably those which are specific to human defensins HNP1-3, such as those described in, *Journal of Immunological Methods*, 141:149–155 (1991). The preferred technique is a mini-plate based assay that utilizes the monoclonal antibody D1-1 to capture defensins HNP1-3, followed by detection, with the monoclonal antibody D1-11 that is labeled with biotin. The monoclonal antibody D1-1 is deposited with the American Type Tissue Collection (10801 University Boulevard, Manassas, Va. USA) and is identified by Accession No. HB 11462.

Antibodies to defensins (D1-1) are added to polystyrene 96-well plates, (Dynex Technologies, Chantilly, Va.) in a 2 µg/100 µL concentration and incubated overnight. The plate may then be washed three (3) times with ddH$_2$O. Prepared samples and standards, diluted in Tris-buffered saline (TBS) with 0.01% CETAB (hexadecyltrimethylammonium bromide) can be added, at 100 µL per well, and incubated for 2 hours at room temperature. Biotinylated monoclonal antibody, preferably in buffer solution, can be added at 100 μL per well, and incubated for 1 hour at room temperature. The plate may then be washed three (3) times with ddH$_2$O. Avidin-peroxidase (ICN Biomedicals, Los Angeles, Calif.) preferably in TBS-1% gelatin may be added at 100 μL per well, and incubated for 1 hour at room temperature. The plate can then be washed three (3) times with ddH$_2$O, prior to adding substrate, preferably 100 μL of OPD (O-phenylenediamine dihydrochloride) (Sigma, St. Louis, Mo.). After 5 minutes, stop solution, preferably 2.5 M sulfuric acid, can be added to terminate the reaction. The absorbance of each well may be read, preferably at 490 nm (Precision Microplate Reader from Molecular Devices, Inc., Sunnyvale, Calif.).

Lactoferrin can be measured, preferably by ELISA. A commercially-available kit, such as LEUKO-ELISA (Techlab, Blacksburg, Va.), specific for lactoferrin, can be used.

Samples and standards may be diluted starting from a 1:20 dilution, preferably with diluent supplied in the kit. To a Microtiter® plate (Dynex Technologies) preferably coated with a polyclonal antibody to human lactoferrin, standard and sample can be added, at 100 μL per well, and incubated for 30 minutes at 37° C. The plate may be washed three (3) times with phosphate buffered saline (PBS) solution. It is preferred that rabbit polyclonal antibody conjugated to horseradish peroxidase be added at 50 μL per well, and the plate may be incubated for 30 minutes at 37° C. The plate may again be washed three (3) times with PBS solution. To each well, 50 μL of tetramethylbenzadine solution and 50 μL of buffered solution containing peroxide may be added and incubated for 15 minutes at room temperature. Stop solution, preferably 1 M sulfuric acid, can then be added to terminate the reaction. The absorbance of each well may be read, preferably at 450 mn (Precision Microplate Reader from Molecular Devices, Inc.).

In a preferred embodiment of the present invention, to screen a pregnant patient for the presence of an intraamniotic infection, amniotic fluid can be removed from a pregnant patient by amniocentesis, preferably prior to the 32$^{nd}$ week of gestation. The concentration of defensins HNP1-3 and the concentration of lactoferrin may be measured, preferably as described herein. It is preferred that the total concentration of defensins, preferably defensins HNP 1-3, measured in the sample be added to the concentration of lactoferrin measured in the sample to yield a measured summed total. This measured summed total can be compared to a known summed total, for patients presenting with an intraamniotic infection. If the measured summed total exceeds the known summed total by a predetermined amount, then a positive indication may preferably be given for the presence of an intraamniotic infection.

Table 1-A summarizes the lactoferrin+defensins levels measured in amniotic fluid samples from those patients who had a positive amniotic fluid culture. At a lactoferrin+defensins level greater than 5000 ng/mL a sensitivity of one hundred percent (100%) and a specificity of eighty-seven percent (87%) resulted. At a lactoferrin+defensins level greater than 7500 ng/mL, the sensitivity decreased to eighty-six percent (86%) but the specificity increased to one hundred percent (100%). At a lactoferrin+defensins level greater than 10,000 ng/mL, the sensitivity further decreased to seventy-one percent (71%) while the specificity remained at one hundred percent (100%). From this data, one skilled in the art will now appreciate that in this situation, a summed total of 7500 ng/mL can be selected as a cutoff value to screen for the presence of an intraamniotic infection, because this value, in this case, lead to the best balance between sensitivity and specificity and yielded a positive predictive value of one hundred percent (100%) and a negative predictive value of ninety-six percent (96%) for these data. Hence, when employing the methods of the present invention, with this data, one could select 7500 ng/mL as a known summed total, for these data, indicative of intraamniotic infection, to be used as a baseline against which to correlate summed totals for sample of patients being screened for the disorder. Depending on the available data and degree of sensitivity and specificity desired, other known summed totals can be employed, as will now be apparent to those of ordinary skill in the art. The exact known summed totals selected is left to the sound discretion of the practitioner, depending on the available data.

Table 1-B summarizes measurements of lactoferrin and defensins levels measured in amniotic fluid samples from those patients who had either a positive amniotic fluid culture or a negative culture with significant placental histology. As can be seen in Table 1-B, a lactoferrin+defensins level greater than 2000 ng/mL resulted in a sensitivity of eighty-seven percent (87%) and a specificity of seventy-three percent (73%). A lactoferrin+defensins level greater than 3000 ng/mL resulted in an eighty percent (80%) sensitivity and an eighty percent (80%) specificity. A lactoferrin+defensins level greater than 5000 ng/mL resulted in a decreased sensitivity of sixty percent (60%) but an increased specificity of ninety-three percent (93%).

In another embodiment of the present invention to screen a patient for the presence of bacterial meningitis, cerebrospinal fluid can be collected from a patient, preferably by means of a lumbar puncture. The concentration of defensins HNP1-3 and the concentration of lactoferrin may be measured, preferably as described above. It is preferred that the concentration of defensins, preferably defensins HNP1-3, measured in the sample be added to the concentration of lactoferrin measured in the sample to yield a measured summed total. This measured summed total can be compared to a known summed total, preferably for patients presenting with bacterial meningitis. If the measured summed total exceeds the known summed total by a predetermined amount, then a positive indication may preferably be given for the presence of bacterial meningitis.

Table 2 summarizes measurements, made in cerebrospinal fluid samples from children suspected of having bacterial meningitis, of standard CSF parameters, defensins levels, lactoferrin levels, and lactoferrin+defensins levels,. As can be seen from Table 2, the optimum level of sensitivity and specificity for the standard CSF parameters was achieved by using the tests in combination, yielding a sensitivity of ninety-five percent (95%) and a specificity of ninety-five percent (95%). The threshold values given for defensins, lactoferrin and defensins were one (1), two (2) and three (3) standard deviations above the levels of the respective peptides measured in patients with viral (aseptic) meningitis. At a level of greater than 3700 ng/mL, the sensitivity and specificity of the defensins+lactoferrin method exceeded the sensitivity and specificity of the standard CSF tests when used in combination. At a defensins+lactoferrin level of greater than 4916 ng/mL, the sensitivity, specificity, positive predictive value and negative predictive value were all one hundred percent (100%). One skilled in the art will now appreciate that the screening test of the present invention becomes a diagnostic test for bacterial meningitis at this level, because it surpasses the current "gold standard" diagnostic test in terms of sensitivity, specificity, positive predictive value and negative predictive value.

In yet another embodiment of the present invention to screen a patient for the presence of sexually transmitted diseases including gonorrhea, chlamydia and trichomoniasis, vaginal fluid may preferably be used. The combined concentrations of defensins HNP 1-3 and lactoferrin may be measured, preferably as described above. It is preferred that the concentration of defensins, preferably defensins HNP 1-3, measured in the sample be added to the concentration of lactoferrin measured in the sample to yield a measured summed total. This measured summed total can be compared to a known summed total for patients presenting with sexually transmitted diseases including gonorrhea, chlamydia and trichomoniasis. If the measured summed total exceeds the known summed total by a predetermined amount, then a positive indication may preferably be given for the presence of the sexually transmitted diseases; gonorrhea, chlamydia and trichomoniasis. Preferably, the known summed totals are prepared for each set of disorders of interest using statistically significant numbers of patients and by employing acceptable statistical sampling methods known in the art.

Table 3 summarizes measurements of lactoferrin and defensins in screening for the sexually transmitted diseases, gonorrhea, chlamydia and trichomoniasis. A lactoferrin level greater than 400 ng/mL had a sensitivity of eighty percent (80%) and a specificity of fifty-five percent (55%). A defensins level greater than 1100 ng/mL had a sensitivity of seventy-eight percent (78%) and a specificity of fifty-five percent (55%). Measuring a sample for either a lactoferrin level greater than 400 ng/mL or a defensins level greater than 100 ng/mL had an increased sensitivity of eighty-eight percent (88%) but a lower specificity of only forty-one percent (41%). Measuring a sample for both a lactoferrin level greater than 400 ng/mL and a defensins level greater than 1100 ng/mL had a sensitivity and a specificity of seventy percent (70%). This combination of defensins and lactoferrin levels had a relatively low positive predictive value of only thirty-six percent (36%) but a relatively high negative predictive value of ninety percent (90%), and can be useful in sparing those likely to be disease-free from further testing.

Another embodiment of the present invention is a dipstick-based kit, suitable for home testing for sexually transmitted diseases. Such a screening test would provide convenience, privacy and eliminate the necessity and cost of visiting a physician for a screening test, although the dipstick kit could also be used in a clinical setting. The dipstick kit would be similar to home pregnancy tests, known to those skilled in the art, and would provide a color indication for the presence of sexually transmitted diseases, based upon the sunnmed levels of defensins and lactoferrin in the sample. Such a dipstick-based kit could be provided with a small plastic cup for collecting and retaining the sample and for conducting the test. A swab could also be provided with the test kit to allow for sampling from the preferred site of the vaginal introitus. The vaginal introitus is preferred so that the specimen can be taken without a speculum and without the aid of a physician. For example, a dipstick can utilize the levels given in Table 3, to preferably provide a positive color reaction for a defensins level above 1100 ng/mL and preferably a different color reaction for a lactoferrin level above 400 ng/mL. When both levels are exceeded, the positive color reactions will combine to yield a third color that is easily distinguishable from the others. A dipstick which turns yellow when a defensins level above 1100 ng/mL is measured, and which turns blue when a lactoferrin level above 400 ng/mL is measured, will turn green when both levels are exceeded, thus correlating the total defensins+ lactoferrin level to one or more of the sexually transmitted diseases, gonorrhea, chlamydia and trichomoniasis. Because a dipstick-based assay kit would be relatively resistant to temperature and humidity variations, it could be easily transported, stored and used virtually anywhere in the world. Such a screening method would have profound implications, especially in Third World countries that currently use the World Health Organization algorithm, with its inherent limitations, to screen for sexually transmitted diseases. Such a use of the method of the present invention, would result in many people, wrongly thought to be disease-free, being effectively treated, thereby reducing the number of disease carriers and incidence of sexually transmitted diseases.

A dipstick-based assay, similar to that described above, could find use in a clinical setting by quickly and reliably indicating bacterial meningitis, using levels from Table 2, or an intraamniotic infection, using levels from Table 1-A, at bedside, immediately upon withdrawal of the fluid sample. This could save valuable time by allowing the physician to initiate treatment sooner, thereby minimizing the harmful effects of the disease.

In another embodiment the method of the present invention may be utilized in combination with a densitometer in a device for use in a setting such as a doctor's office, a clinic or a hospital. The densitometer can provide rapid measurement of the optical density of dipstick strips, that have been contacted with a bodily fluid or tissue, to screen for inflammatory diseases using the method disclosed by the present invention.

Other possible approaches include the use of electrochemical sensor strips, such as those used for home glucose testing, onto which a sample is placed, and which strips include reagents for initiating a reaction when wetted by the sample. The sensor strip is inserted into a meter which measures, e.g., diffusion-limited current of a reaction species indicative of the analyte of interest, in this case lactoferrin and defensins. The meter then yields a display indicative of the concentration of analyte in the sample.

The foregoing illustrations of embodiments of the present invention are offered for purposes of illustration and not limitation. It will be readily apparent to those skilled in the art that the embodiments described herein may be modified or revised in various ways without departing from the spirit and scope of the invention. The scope of the invention is to be measured by the appended claims.

TABLE 1-A

| Lactoferrin + Defensins Level | Intraamniotic Infection Culture Positive at <32 Weeks (n = 30) | | | |
|---|---|---|---|---|
| | Sensitivity | Specificity | Positive Predictive Value | Negative Predictive Value |
| >5000 ng/mL | 100% | 87% | 70% | 100% |
| >7500 ng/mL | 86% | 100% | 100% | 96% |
| >10,000 ng/mL | 71% | 100% | 100% | 92% |

TABLE 1-B

Intraamniotic Infection
Any Infected at <32 Weeks
(n = 30)

| Lactoferrin + Defensins Level | Sensitivity | Specificity | Positive Predictive Value | Negative Predictive Value |
|---|---|---|---|---|
| >2000 ng/mL | 87% | 73% | 76% | 85% |
| >3000 ng/mL | 80% | 80% | 80% | 80% |
| >5000 ng/mL | 60% | 93% | 90% | 70% |

Combination of lactoferrin and defensins in patient samples.

"Culture positive" are those with a positive amniotic fluid culture.

"Any infected" are culture positive or culture negative but with significant placental histology.

TABLE 2

Bacterial Meningitis

| | Sensitivity | Specificity | Positive Predictive Value | Negative Predictive Value |
|---|---|---|---|---|
| Standard CSF studies | | | | |
| Positive CSF Gram stain | 84% | 100% | 100% | 96% |
| CSF White Blood Cells > 1000 | 53% | 100% | 100% | 88% |
| CSF glucose < 30 mg/dL | 58% | 98% | 92% | 89% |
| CSF protein > 100 mg/dL | 90% | 97% | 90% | 97% |
| Any of the above | 95% | 95% | 86% | 98% |
| Defensins Levels | | | | |
| >670 ng/mL | 95% | 94% | 82% | 98% |
| >1093 ng/mL | 95% | 95% | 86% | 98% |
| >1526 ng/mL | 90% | 98% | 94% | 97% |
| Lactoferrin Levels | | | | |
| >1920 ng/mL | 90% | 89% | 71% | 97% |
| >2798 ng/mL | 84% | 100% | 100% | 95% |
| >3676 ng/mL | 84% | 100% | 100% | 95% |
| Defensins + Lactoferrin | | | | |
| >2484 ng/mL | 100% | 91% | 76% | 100% |
| >3700 ng/mL | 100% | 97% | 91% | 100% |
| >4916 ng/mL | 100% | 100% | 100% | 100% |

Threshold values were 1, 2, and 3 standard deviations of the levels in patients with viral meningitis.

TABLE 3

Sexually Transmitted Diseases

| Criteria: | Sensitivity | Specificity | Positive Predictive Value | Negative Predictive Value |
|---|---|---|---|---|
| Lactoferrin > 400 ng/mL | 80% | 55% | 31% | 92% |
| Defensins > 1100 ng/mL | 78% | 55% | 30% | 92% |
| Lactoferrin > 400 ng/mL or Defensins > 1100 ng/mL | 88% | 41% | 27% | 93% |
| Lactoferrin > 400 ng/mL and Defensins > 1100 ng/mL | 70% | 70% | 36% | 90% |

I claim:

1. A method of evaluating a patient for the presence of one or more inflammatory disorders of said patient, said method comprising the steps of:
   determining a summed total of concentrations of defensins and lactoferrin in a sample of said patient; said sample comprising a bodily fluid, a tissue or a combination thereof; and,
   correlating said summed total of concentrations of defensins and lactoferrin in said sample with at least one known summed total of concentrations of defensins and lactoferrin indicative of said one or more said inflammatory disorders.

2. The method of claim 1, wherein the steps of determining and correlating are accomplished by a dipstick.

3. The method of claim 1, wherein the steps of determining and correlating are accomplished by a densitometer.

4. The method of claim 1, wherein the steps of determining and correlating are accomplished by an electrochemical sensor strip.

5. The method of claim 1, wherein the step of determining said summed total of concentrations of defensins and lactoferrin in said sample comprises:
   contacting a portion of said sample with an anti-defensins antibody for a time sufficient to permit antigen-antibody binding to occur;
   assaying the amount of said defensins present;
   contacting a portion of said sample with an anti-lactoferrin antibody for a time sufficient to permit antigen-antibody binding to occur;
   assaying the amount of said lactoferrin present; and,
   adding the assayed said amount of defensins to the assayed said amount of lactoferrin to yield said summed total of concentrations of defensins and lactoferrin in said sample.

6. A method of screening a patient for the presence of one or more inflammatory disorders using a sample taken from said patient; said sample comprising a bodily fluid, a tissue or a combination thereof; said method comprising the steps of:
   determining a summed total of concentrations of lactoferrin and at least one member selected from the group consisting of: human neutrophil peotides HNP1, HNP2, HNP3, HNP4, HNP5, human defensins HD-5, HD-6, human β defensins HBD-1, and HBD-2 in said sample; and,
   correlating said summed total of concentrations of said lactoferrin and the at least one member of the group consisting of: human neutrophil peptides HNP1, HNP2, HNP3, HNP4, HNP5, human defensins HD-5, HD-6human β defensins HBD-1, and HBD-2 in said sample with at least one known corresponding summed total of concentrations of lactoferrin and at least one member of the group consisting of: human neutrophil peptides HNP1, HNP2, HNP3, HNP4, HNP5, human defensins HD-5, HD-6, human β defensins HBD-1, and HBD-2 indicative of said one or more said inflammatory disorders.

7. A method of screening a patient for the presence of one or more disorders selected from the group consisting of: intraamniotic infection, bacterial meningitis, gonorrhea, chlamydia and trichomoniasis, using a sample taken from patient said sample comprising a bodily fluid, a tissue or a combination thereof; said method comprising the steps of:
   determining a summed total of concentrations of defensins and lactoferrin in said sample; and,
   correlating said summed total of concentrations of defensins and lactoferrin in said sample with at least one known summed total of concentrations of defensins and lactoferrin indicative of said one or more disorders.

8. The method of claim 7, wherein the step of determining said summed total of concentrations of defensins and lactoferrin in said sample comprises:

contacting a portion of said sample with an anti-defensins antibody for a time sufficient to permit antigen-antibody binding to occur;

assaying the amount of said defensins present;

contacting a portion of said sample with an anti-lactoferrin antibody for a time sufficient to permit antigen-antibody binding to occur;

assaying the amount of said lactoferrin present; and, adding the assayed said amount of defensins to the assayed said amount of lactoferrin to yield said summed total of concentrations of defensins and lactoferrin in said sample.

9. A method of screening a patient for the presence of one or more inflammatory disorders using a sample taken from said patient; said sample comprising a bodily fluid, a tissue or a combination thereof; said method comprising the steps of:

determining a summed total of concentrations of human neutrophil peptides and lactoferrin in said sample; and, correlating said summed total of human neutrophil peptides and lactoferrin in said sample with at least one known summed total of human neutrophil peptides and lactoferrin indicative of said one or more said inflammatory disorders.

10. The method of claim 9, wherein the step of determining said summed total of concentrations of human neutrophil peptides and lactoferrin in said sample comprises:

contacting a portion of said sample with an anti-human neutrophil peptide antibodies for a time sufficient to permit antigen-antibody binding to occur;

assaying the amount of said human neutrophil peptides present;

contacting a portion of said sample with an anti-lactoferrin antibody for a time sufficient to permit antigen-antibody binding to occur;

assaying the amount of said lactoferrin present; and, adding the assayed said amount of human neutrophil peptides to the assayed said amount of lactoferrin to yield said summed total of concentrations of human neutrophil peptides and lactoferrin in said sample.

11. A method of screening a patient for the presence of one or more inflammatory disorders using a sample taken from said patient; said sample comprising a bodily fluid, a tissue or a combination thereof; said method comprising the steps of:

determining the concentrations of human neutrophil peptides and lactoferrin in said sample;

adding the determined concentrations of human neutrophil peptides and lactoferrin together to produce a summed total of human neutrophil peptides and lactoferrin for said sample; and, correlating said summed total of human neutrophil peptides and lactoferrin for said sample with known summed totals of human neutrophil peptides and lactoferrin indicative of said one or more inflammatory disorders.

12. The method of claim 11, wherein the step of determining concentrations of said human neutrophil peptides and lactoferrin in said sample comprises:

contacting a portion of said sample with anti-human neutrophil peptide antibodies for a time sufficient to permit antigen-antibody binding to occur;

assaying the amount of said human neutrophil peptides present;

contacting a portion of said sample with an anti-lactoferrin antibody for a time sufficient to permit antigen-antibody binding to occur; and, assaying the amount of said lactoferrin present.

13. A method of screening a patient for the presence of one or more inflammatory disorders in a sample taken from said patient; said sample comprising a bodily fluid, a tissue or a combination thereof, said method comprising the steps of:

determining concentrations of human neutrophil peptides and lactoferrin in said sample;

adding the determined concentrations of human neutrophil peptides and lactoferrin together to produce a summed total for the sample;

comparing said summed total for said sample to a corresponding known reference summed total of human neutrophil peptides and lactoferrin; and, if said summed total for the sample exceeds said known reference summed total by at least a predetermined amount, correlating said summed total for the sample exceeding said known reference summed total with known corresponding abnormal summed totals indicative of said one or more said inflammatory disorders, thereby providing a positive screen for said one or more disorders.

14. The method of claim 13, wherein the step of determining concentrations of said human neutrophil peptides and lactoferrin in said sample comprises:

contacting a portion of said sample with anti-human neutrophil peptide antibodies for a time sufficient to permit antigen-antibody binding to occur;

assaying the amount of said human neutrophil peptides present;

contacting a portion of said sample with an anti-lactoferrin antibody for a time sufficient to permit antigen-antibody binding to occur; and, assaying the amount of said lactoferrin present.

15. A method of screening for the presence of one or more inflammatory disorders in a patient, said method comprising:

obtaining a sample comprising a bodily fluid, a tissue or a combination thereof from said patient;

determining concentrations of human neutrophil peptides and lactoferrin in said sample;

adding the determined concentrations of human neutrophil peptides and lactoferrin together to produce a summed total for said sample;

comparing said summed total of human neutrophil peptides and lactoferrin for said sample to a corresponding known reference summed total of human neutrophil peptides and lactoferrin; and, if said summed total of human neutrophil peptides and lactoferrin for said sample exceeds said known reference summed total of human neutrophil peptides and lactoferrin by at least a predetermined amount, correlating said summed total of human neutrophil peptides and lactoferrin for said sample exceeding said known reference summed total of human neutrophil peptides and lactoferrin with corresponding known abnormal summed totals of human neutrophil peptides and lactoferrin indicative of said one or more said inflammatory disorders, thereby providing a positive screen for said one or more disorders.

16. The method as in any one of claims 1 or 6 in which said sample is amniotic fluid and said one or more disorders is an intraamniotic infection.

17. The method as in any one of claims 1 or 6 in which said sample is cerebrospinal fluid and said one or more disorders is ,bacterial meningitis.

18. The method as in any one of claims 1 or 6 in which said sample is vaginal fluid and said one or more disorders is selected from the group consisting of gonorrhea, chlamydia and trichomoniasis.

19. The method of claim 15, wherein the step of determining concentrations of said human neutrophil peptides and lactoferrin in said sample comprises:

contacting a portion of said sample with anti-human neutrophil peptide antibodies for a time sufficient to permit antigen-antibody binding to occur;

assaying the amount of said human neutrophil peptides present;

contacting a portion of said sample with an anti-lactoferrin antibody for a time sufficient to permit antigen-antibody binding to occur; and, assaying the amount of said lactoferrin present.

20. A method of screening a patient for the presence of bacterial meningitis using a sample taken from said patient; said sample comprising a bodily fluid, a tissue or a combination thereof; said method comprising the steps of:

determining a summed total of concentrations of lactoferrin and at least one member selected from the group consisting of: human neutrophil peptides HNP1, HNP2, HNP3, HNP4, HNP5, human defensins HD-5, HD-6, human β defensins HBD-1, and HBD-2 in said sample; and,correlating said summed total of concentrations of said lactoferrin and the at least one member of the group consisting of: human neutrophil peptides HNP1, HNP2, HNP3, HNP4, HNP5, human defensins HD-5, HD-6, human β defensins HBD-1, and HBD-2 in said sample with at least one known corresponding summed total of concentrations of lactoferrin and at least one member of the group consisting of: human neutrophil peptides HNP1, HNP2, HNP3, HNP4, HNP5, human defensins HD-5, HD-6, human β defensins HBD-1, and HBD-2 indicative of bacterial meningitis, wherein said steps of determining and correlating are accomplished by a dipstick.

21. A method of screening a patient for the presence of bacterial meningitis using a sample taken from said patient, said method comprising:

contacting a portion of said sample with anti-human neutrophil peptide antibodies for a time sufficient to permit antigen-antibody bonding to occur;

assaying the amount of said human neutrophil peptides present;

contacting a portion of said sample with an anti-lactoferrin antibody for a time sufficient to permit antigen-antibody binding to occur;

assaying the amount of said lactoferrin present;

adding the assayed said amount of human neutrophil peptides to the assayed said amount of lactoferrin to yield a summed total of concentrations of human neutrophil peptides and lactoferrin in said sample; and, correlating said summed total of concentrations of human neutrophil peptides and lactoferrin in said sample with at least one known corresponding summed total of human neutrophil peptides and lactoferrin indicative of bacterial meningitis, wherein said steps are accomplished by a dipstick.

22. The method of claim 21, wherein said sample comprises cerebrospinal fluid.

* * * * *

UNITED STATES PATENT AND TRADEMARK OFFICE
CERTIFICATE OF CORRECTION

PATENT NO.    : 6,174,664 B1
DATED         : January 16, 2001
INVENTOR(S)   : Heine It is certified that error appears in the above-identified patent and that said Letters Patent is hereby corrected as shown below:

Column 2,
Line 31, delete the digits "35" before "irritability"

Column 3,
Line 59, delete "Chlamvdia" and insert in its place -- Chlamydia --

Column 7,
Line 35, delete "mn" and insert in its place -- nm --

Column 12,
Line 13, delete "electrochemical" and insert in its place -- electro-chemical --
Line 37, delete "peotides" and insert in its place -- peptides --
Line 41, delete word "said" and insert in its place -- the --
Line 53, insert "inflammatory" before "disorders"
Line 57, insert -- ; -- following "patient" and before "said sample"

Column 14,
Line 62, delete "said inflammatory"
Line 64, insert "said inflammatory" following "one or more"

Signed and Sealed this

Nineteenth Day of March, 2002

Attest:

JAMES E. ROGAN
*Attesting Officer*   *Director of the United States Patent and Trademark Office*